United States Patent
Dettinger et al.

(10) Patent No.: US 7,693,857 B2
(45) Date of Patent: Apr. 6, 2010

(54) CLINICAL GENOMICS MERGED REPOSITORY AND PARTIAL EPISODE SUPPORT WITH SUPPORT ABSTRACT AND SEMANTIC MEANING PRESERVING DATA SNIFFERS

(75) Inventors: Richard D. Dettinger, Rochester, MN (US); Thomas J. Eggebraaten, Rochester, MN (US); Daniel P. Kolz, Rochester, MN (US); Richard J. Stevens, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 785 days.

(21) Appl. No.: 11/282,094

(22) Filed: Nov. 17, 2005

(65) Prior Publication Data
US 2007/0112586 A1    May 17, 2007

(51) Int. Cl.
*G06F 7/00* (2006.01)
*G06F 17/30* (2006.01)
*G06Q 50/00* (2006.01)

(52) U.S. Cl. .............. 707/101; 707/104.1; 705/1; 705/2

(58) Field of Classification Search .......... 707/1, 707/8–10, 100, 101, 104.1, 200–204; 705/1, 705/2
See application file for complete search history.

(56) References Cited

U.S. PATENT DOCUMENTS

| 5,991,758 | A | * | 11/1999 | Ellard ..................... 707/6 |
| 6,039,688 | A | * | 3/2000 | Douglas et al. ........... 600/300 |
| 6,047,259 | A | * | 4/2000 | Campbell et al. .......... 705/3 |
| 6,725,227 | B1 | | 4/2004 | Li |
| 7,389,245 | B1 | * | 6/2008 | Ashford et al. ........... 705/2 |
| 2002/0174142 | A1 | * | 11/2002 | Demers et al. ........... 707/509 |
| 2002/0194028 | A1 | * | 12/2002 | Johnston et al. .......... 705/3 |
| 2003/0216945 | A1 | * | 11/2003 | Dvorak et al. ............ 705/3 |
| 2004/0044546 | A1 | * | 3/2004 | Moore .................... 705/2 |
| 2004/0215618 | A1 | * | 10/2004 | Wacke et al. ............. 707/10 |
| 2004/0220836 | A1 | * | 11/2004 | Doherty et al. ........... 705/3 |
| 2004/0225641 | A1 | * | 11/2004 | Dettinger et al. ......... 707/3 |
| 2005/0027578 | A1 | * | 2/2005 | Chambers et al. ......... 705/8 |
| 2005/0198564 | A1 | * | 9/2005 | Sinzig et al. ............ 715/507 |
| 2006/0117238 | A1 | * | 6/2006 | DeVries et al. .......... 714/746 |

FOREIGN PATENT DOCUMENTS

WO    WO 03085577 A1 * 10/2003
WO    WO 2004063907 A2 *  7/2004

* cited by examiner

Primary Examiner—John R. Cottingham
Assistant Examiner—James E Richardson
(74) Attorney, Agent, or Firm—Patterson & Sheridan, LLP

(57) ABSTRACT

Method, apparatus and article of manufacture for processing and storing medical episode data with workflow status designations. In one embodiment, a patient episode data is moved from differentiated data stores, via an information broker, to assigned data handlers. The data handlers then pass their respective data to a loader and shredder application. The shredder application is tasked with storing the episode data in the database repository and updating each episode's status.

9 Claims, 8 Drawing Sheets

CLINICAL GENOMICS MERGED REPOSITORY AND PARTIAL EPISODE SUPPORT WITH SUPPORT ABSTRACT AND SEMANTIC MEANING PRESERVING DATA SNIFFERS

BACKGROUND OF THE INVENTION

1. Field of the Invention

The present invention is generally directed to a method, system and article of manufacture for importing various clinical genomic data directly into a central database to enable the data to be accessed on-demand by queries.

2. Description of the Related Art

Databases are computerized information storage and retrieval systems. A relational database management system (RDBMS) is a computer database management system that uses relational techniques for storing and retrieving data. Relational databases are computerized information storage and retrieval systems in which data in the form of tables (formally denominated "relations") are typically stored for use on disk drives or similar mass data stores. A "table" includes a set of rows (formally denominated "tuples" or "records") spanning several columns (formally denominated "attributes").

A RDBMS is structured to accept commands to store, retrieve and delete data using, for example, high-level query languages such as the Structured Query Language (SQL). The term "query" denominates a set of commands for retrieving data from a stored database. These queries may come from users, application programs, or remote systems (clients or peers). The query language requires the return of a particular data set in response to a particular query but the method of query execution ("Query Execution Plan") employed by the RDBMS is not specified by the query. The method of query execution is typically called an execution plan, an access plan, or just "plan". There are typically many different useful execution plans for any particular query, each of which returns the required data set. For large databases, the execution plan selected by the RDBMS to execute a query must provide the required data at a reasonable cost in time and hardware resources.

For the capture and processing of complex data from a plurality of different data sources, it is common to set up a staging data store and an operational database. The staging data store's function is to buffer related data from different data sources until a condition is satisfied, at which point the related data is processed and migrated from the staging data store to the operation database via a set of data transformations.

In a clinical genomics application, medical information from a variety of data sources for a given patient are stored in a staging data store (which may be referred to as the "Medical Information Gateway" or "MIG"). A given series of related data, called "events", are grouped together into an "episode". In one embodiment, an event in the MIG might contain lab work data, disease presentation data, or other crucial patient information. Once all events of a given episode are complete the system processes and imports the data into the operational database (the "Medical Information Repository" or "MIR"). Thus, the condition that triggers migration of the event data from the MIG to the MIR is the completion of the corresponding episode.

A problem arises with this arrangement when queries that require real-time data are run against the operational database. Because the affiliated data for a particular episode is not imported into the operation database until all associated events or steps are completed, data that could be critical to patient well-being may not be available in the operational database for queries. In other words, crucial patient data is not available to queries because all events in an episode are not yet complete and so the data has not been moved from the MIG into the MIR.

An existing solution to the problem has been obtained by using "sniffers" to analyze data within the MIG data store for specific conditions. Sniffers are computerized information analyzing and retrieval applications. Typically, a sniffer is created to locate data in a particular database or data store, following a very specific set of analysis rules and stored for use on disk drives or similar mass data stores. If the conditions are met, the sniffer fires actions according to its rule sets. Using sniffers to locate data in the staging data store is complicated by the fact that the staging data store contains different data types that are not all accessible by a single sniffer. As a result, a unique sniffer is needed for each type of data to be stored in the staging data store or MIG.

Accordingly, there is a need for a staged data environment in which related data pertaining to ongoing episodes can be accounted for in a query result in real-time.

SUMMARY OF THE INVENTION

The present invention generally is directed to a method, system, and article of manufacture for storing status-designated health-related data in an operational database.

One embodiment provides a method for storing status-designated health-related data. The method generally includes providing a database which stores health-related episode data from a plurality of data sources. The episode data may include data for complete episodes and incomplete episodes, an episode being defined by a predefined set of related data. A plurality of updates to the episode data corresponding to the incomplete episodes may be received. For each of the plurality of updates, the status of episode data being updated in the database may be designated as either complete or incomplete.

Another embodiment provides a tangible computer-readable storage medium containing a program. When executed by a processor, the program performs operations including storing status-designated health-related episode data. A plurality of updates to health-related episode data corresponding to an incomplete episode may be received. For each of the plurality of updates, the status of episode data being updated in the database may be designated as either complete or incomplete. The episode data may be contained in a database which stores the episode data from a plurality of data sources. The episode data includes data for complete episodes and incomplete episodes.

Another embodiment provides a database system for storing status-designated health-related episode data. The database system generally includes an operational datastore and a status monitor. The operational datastore can be configured to receive new episode data from a plurality of external datastores. The episode is defined by a predefined set of related data. The new episode data may be stored in a data structure in the operational datastore. The status monitor may be configured to monitor a status of the episode data in the operational datastore and apply the status to the data in the operational datastore responsive to the new episode data being received.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Figure 1:
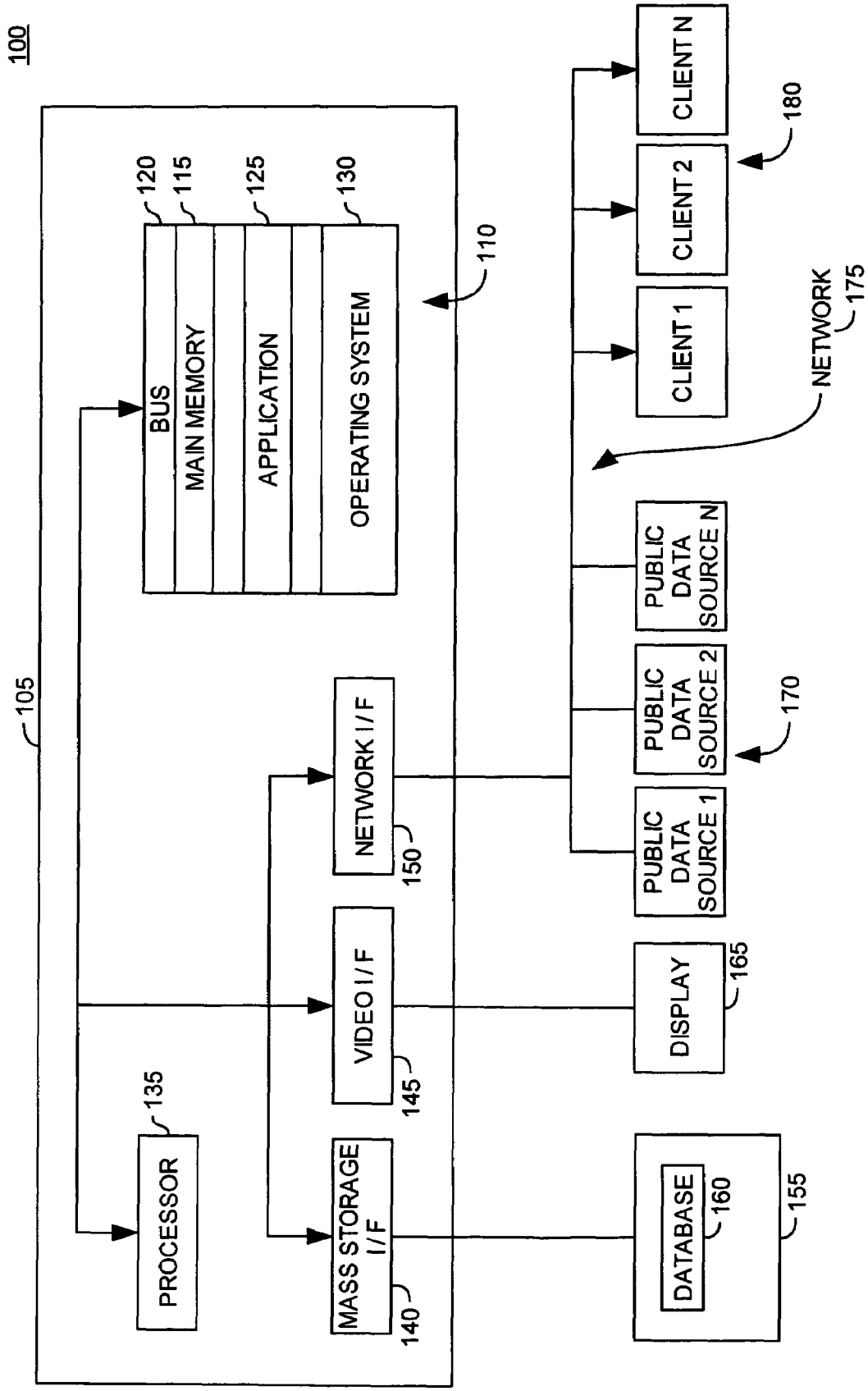
FIG. 1 is a general purpose computer system illustratively utilized in accordance with the invention.

The present invention generally is directed to a system, method and article of manufacture for processing and storing medical episode data with workflow status information. In one embodiment, a patient episode data is moved from differentiated data stores, via an information broker, to assigned data handlers. The data handlers then pass their respective data to a loader and shredder application. The shredder application is tasked with storing the episode data in the database repository and updating each episode's status. In one embodiment, a data repository abstraction layer provides a logical view of the underlying data repository that is independent of the particular manner of data representation. A query abstraction layer may be provided and is based on the data repository abstraction layer. A runtime component performs translation of an abstract query into a form that can be used against a particular physical data representation.

One embodiment of the invention is implemented as a program product for use with a computer system such as, for example, the computer system 100 shown in FIG. 1 and described below. The program(s) of the program product defines functions of the embodiments (including the methods described herein) and can be contained on a variety of signal-bearing media. Illustrative signal-bearing media include, but are not limited to: (i) information permanently stored on non-writable storage media (e.g., read-only memory devices within a computer such as CD-ROM disks readable by a CD-ROM drive); (ii) alterable information stored on writable storage media (e.g., floppy disks within a diskette drive or hard-disk drive); or (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The software of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular nomenclature that follows is used merely for convenience, and thus the invention should not be limited to use solely in any specific application identified and/or implied by such nomenclature.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Physical View of Environment

Referring now to FIG. 1, a computing environment 100 is shown. In general, the distributed environment 100 includes a computer system 105 and a plurality of networked devices 175. The computer system 105 may represent any type of computer, computer system or other programmable electronic device, including a client computer, a server computer, a portable computer, an embedded controller, a PC-based server, a minicomputer, a midrange computer, a mainframe computer, and other computers adapted to support the methods, apparatus, and article of manufacture of the invention. In one embodiment, the computer system 26 is an eServer iSeries available from International Business Machines of Armonk, N.Y.

Illustratively, the computer system 105 comprises a networked system. However, the computer system 105 may also comprise a standalone device. In any case, it is understood that FIG. 1 is merely one configuration for a computer system. Embodiments of the invention can apply to any comparable configuration, regardless of whether the computer system 100 is a complicated multi-user apparatus, a single-user workstation, or a network appliance that does not have non-volatile storage of its own.

The embodiments of the present invention may also be practiced in distributed computing environments in which tasks are performed by remote processing devices that are linked through a communications network. In a distributed computing environment, program modules may be located in both local and remote memory storage devices. In this regard, the computer system 105 and/or one or more of the networked devices 175 may be thin clients which perform little or no processing.

The computer system 105 could include a number of operators and peripheral systems as shown, for example, by a mass storage interface 140 operably connected to a direct access storage device 155, by a video interface 145 operably connected to a display 165, and by a network interface 175 operably connected to the plurality of networked devices 170 and 180 via a network 175 (e.g. WAN, LAN). The display 165 may be any video output device for outputting viewable information.

Computer system 105 is shown comprising at least one processor 135, which obtains instructions and data via a bus 120 from a main memory 115. The processor 135 could be any processor adapted to support the methods of the invention.

The main memory 115 is any memory sufficiently large to hold the necessary programs and data structures. Main memory 115 could be one or a combination of memory devices, including Random Access Memory, nonvolatile or backup memory, (e.g., programmable or Flash memories, read-only memories, etc.). In addition, memory 115 may be considered to include memory physically located elsewhere in a computer system 105, for example, any storage capacity used as virtual memory or stored on a mass storage device (e.g., direct access storage device 155) or on another computer coupled to the computer system 105 via bus 120.

The memory 115 is shown configured with an operating system 130. The operating system 130 is the software used for managing the operation of the computer system 110. Examples of the operating system 130 include IBM OS/400®, UNIX, Microsoft Windows®, and the like.

The memory 115 further includes one or more applications. The applications 125 are software products comprising a plurality of instructions that are resident at various times in various memory and storage devices in the computer system 110. When read and executed by one or more processors 135 in the computer system 110, the applications 125 cause the computer system 110 to perform the steps necessary to execute steps or elements embodying the various aspects of the invention.

Relational View of Environment

Figure 2:
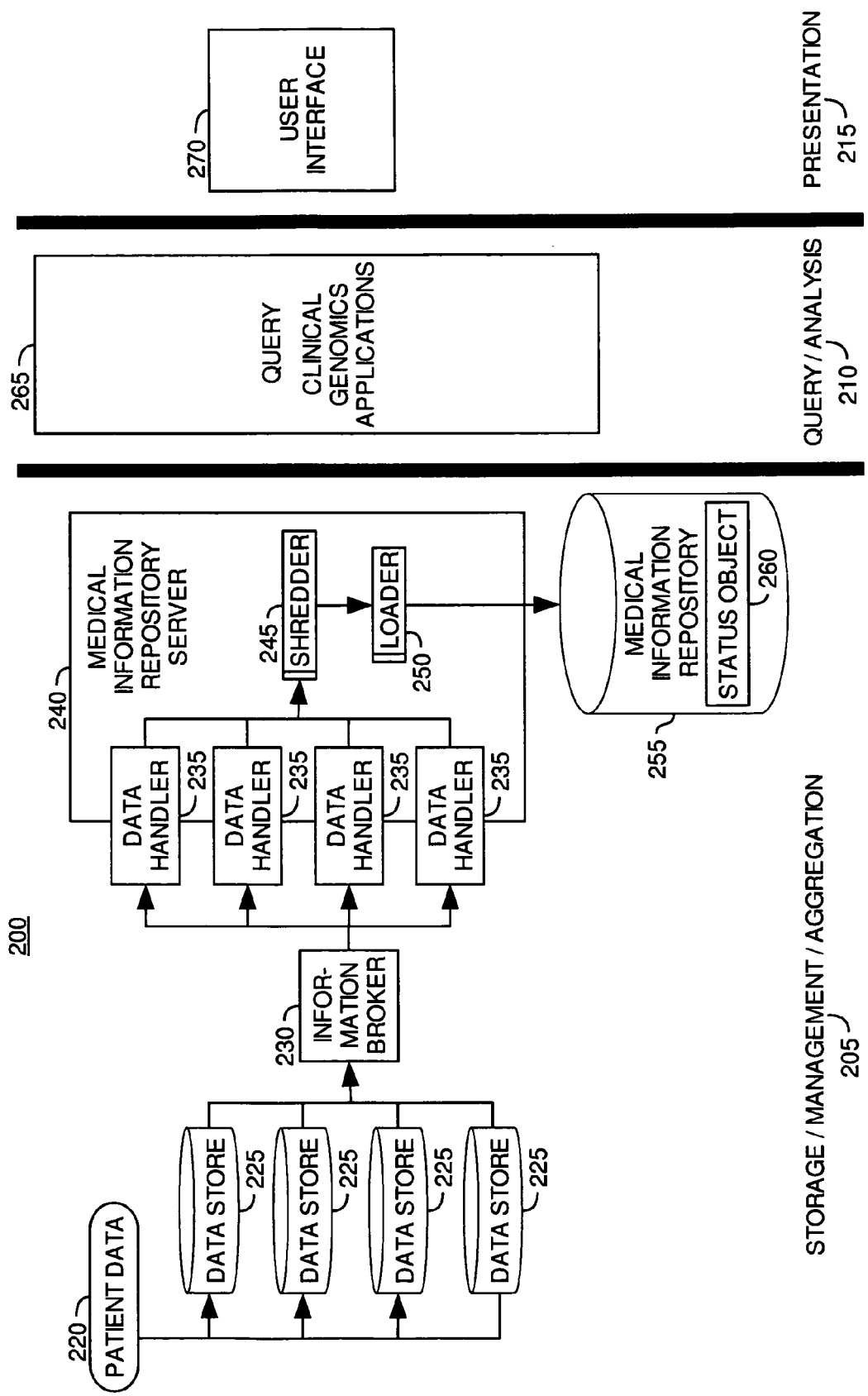
FIG. 2 is a relational view of software components of one embodiment of the invention.

FIG. 2 shows a relational view of a data processing environment 200 of software components of one embodiment of the invention. The data processing environment 200 is generally arranged (logically) into three stages: a storage/management/aggregation stage 205, query/analysis stage 210 and a presentation stage 215. In the storage/management/aggregation stage 205, patient episode data is stored in a plurality of generic data stores $225_1$, $225_2$, $225_3$, $225_4$ (four shown by way of example; collectively referred to as data store 225). In one embodiment, the data store 225 may include any variety of data including pathology data, radiology data, pharmaceutical data, gene expressions, etc. An information broker application 230 is used to transfer episode data from each data store to a specific data handler application. In one embodiment, a plurality of data handlers $235_1$, $235_2$, $235_3$, $235_4$ (four shown by way of example; collectively referred to as data handler 235) receive specific data store data from the information broker 230. The information broker application 230 is a computer software application used to pass data from one data store 225 or application to another application. The data handlers 235 may generally be any computer software applications used to transfer data of a specific schema from location to another (e.g., from the information broker 230 to a target application, such as the shredder application 245 described below).

In one embodiment, the data handlers 235 pass the patient episode data to a shredder application 245 of a medical information repository server 240. The shredding application 245 parses the data files and arranges the data according to a specific schema. Once the shredding process is complete and the data has been normalized in the specific schema, the data is passed to a loader application 250. The loader application 250 analyzes existing patient episode data in the MIR database 255 to determine an appropriate status for the episode data just received from shredding application 245. More specifically, the loader application 250 identifies any existing patient episode data in the MIR database 255 which is related to (i.e., part of the same episode of) the data just received from shredding application 245. In one embodiment, the status of the episodic data in the MIR database 255 is designated as either complete or incomplete. In some instances the data just received from shredding application 245 is the first portion of episodic data related to a given episode, in which case the MIR database 255 will not contain any related data and the status of the received data will be designated as incomplete. In other instances, the data just received from shredding application 245 will be a portion of an episode for which partial episodic data is contained in the MIR database 255, but which does not complete the episode in which case the status of the data is again designated as incomplete. In yet another instance, the data just received from shredding application 245 will be the final portion of an episode for which the remaining episodic data is contained in the MIR database 255, in which case the status of related episodic data defining the episode will be designated as complete.

In one embodiment, if a given patient episode data is incomplete, then the loader application 250 stores the episode data in the MIR database 255 and updates a MIR status object 260 with an incomplete status. If the given patient episode data is complete, then the loader application 250 stores the episode data in the MIR database 255 and updates the MIR status object 260 with a complete status. While this embodiment employs a binary status of incomplete or complete, persons skilled in the art will recognize other embodiments within the scope of the invention. For example, an alternative embodiment may use a lookup table to store a plurality of different statuses. The lookup table could be a database table containing a list of available statuses, such as "episode begun", "episode updated", "episode complete". These statuses would be assigned to a given episode's data in the MIR and could be used to give end users more information as to where a given episode is in its specific workflow process.

Once stored in the MIR database 255, patient episode data is available for querying by an appropriate application in the query/analysis stage 210. In one embodiment, the MIR database 255 is queried using a clinical genomics application 265. The results of queries may be returned to a user in a presentation stage 215 by means of a user interface 270. Other embodiments of a querying environment are described below with reference to FIG. 5a.

Figure 3:
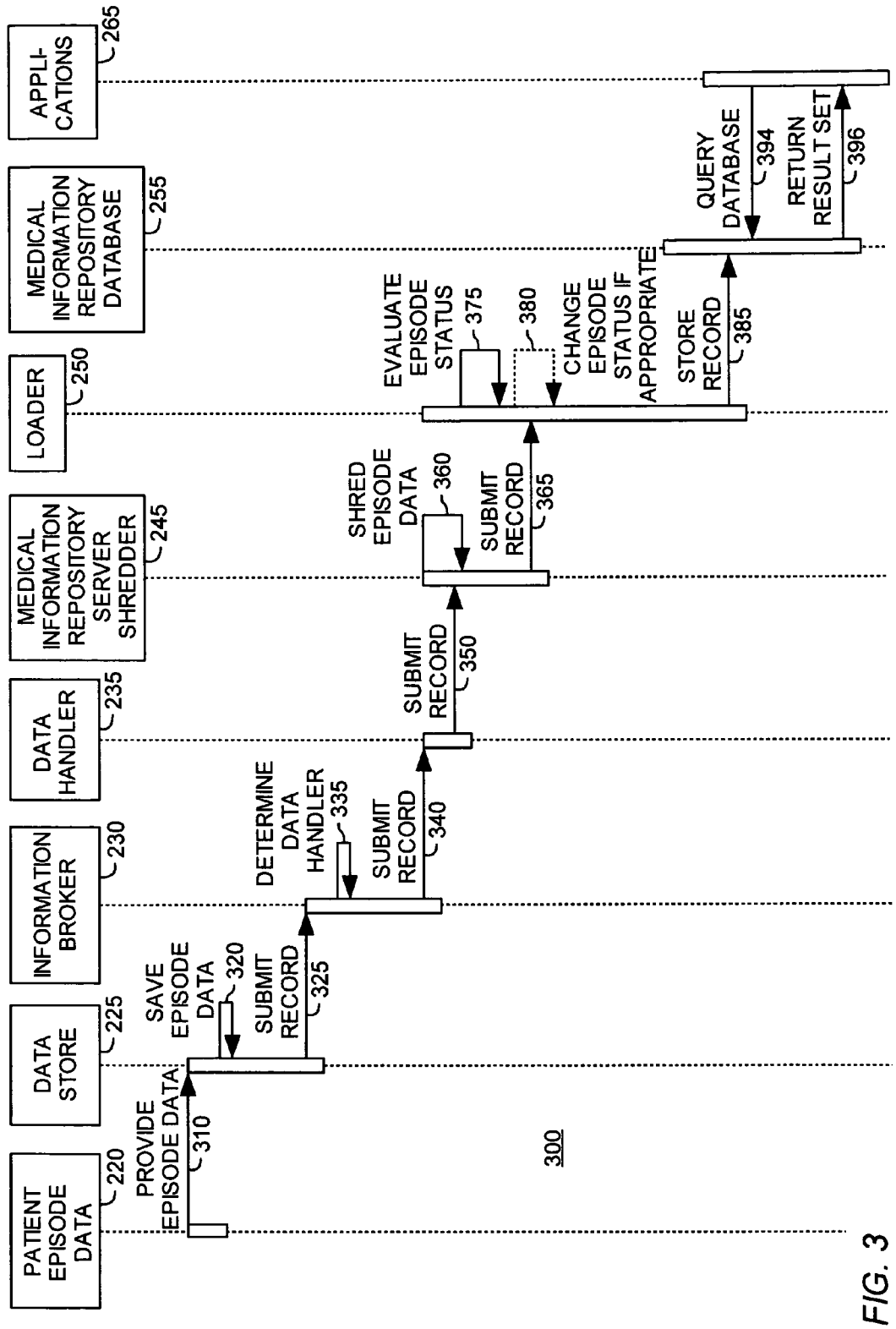
FIG. 3 is a process flow diagram illustrating the operation of one embodiment of the invention.

FIG. 3 is a process flow diagram illustrating the operation 300 of one embodiment of the invention. Components described above with reference will be identified by like reference numbers. Patient episode data 220 is provided (step 310) to the data store 225. The data store 315 saves 320 the episode data and then submits (step 325) the data record to the information broker 230. The information broker 230 analyzes the episode data to determine (step 335) the correct data handler 235 (i.e., the appropriate data handler 235 particularly configured to handle the particular type of episode data received). Once determined, the episode data is submitted (step 335) to the appropriate data handler 235 for further processing. The data handler 235 submits (step 350) the episode data to the medical information repository server shredder 245, which parses/shreds (step 360) the episode data to ensure the data is in the correct schema. The shredder 245 submits (step 365) the data to the loader 250 which evaluates (step 375) the episode completeness status. That is, the loader 250 determines whether the data received from the shredder completes an episode for which related episodic data resides in the medical information repository database 255. If the loader 250 determines that the status of any related episode data (in the medical information repository database 255) has changed, it changes the episode data's status 380. The received episode data is then stored (step 385) in the medical information repository database 255. Once episode data has been stored in the MIR database 255, it may be available for querying (step 394) by a plurality of applications 265. Upon being queried (step 394) by the application 265, the MIR database 255 returns a resultset 396 of episode data.

Figure 4A:
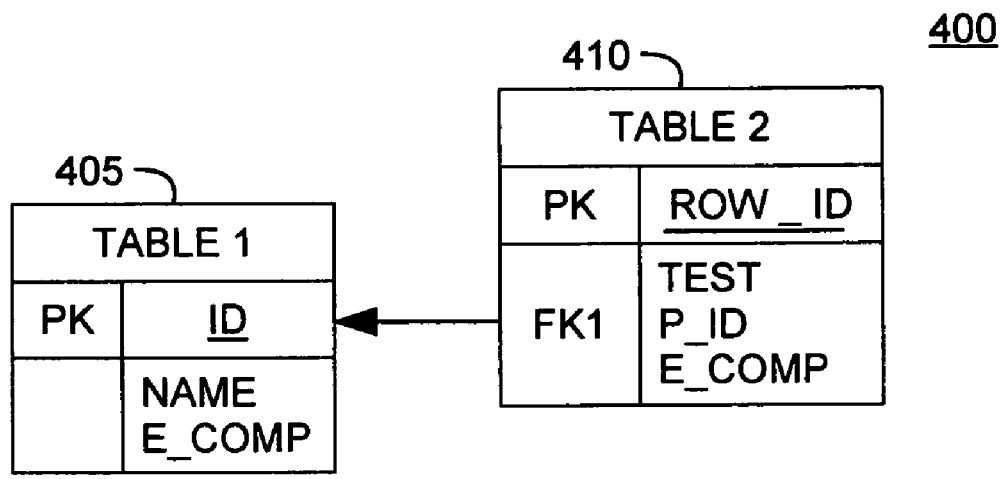
FIG. 4a illustrates an example database schema.

FIG. 4a illustrates an exemplary database schema 400. As used herein, the term "schema" generically refers to a particular arrangement of data. In one embodiment of the invention, database table1 405 contains a primary field ID and a field NAME, and a field E_COMP. Database table2 410 is a child table of table1 405, with a primary field ROW_ID, a field TEST, a foreign key field P_ID, and a field E_COMP. A primary key is a column in a table whose values uniquely identify rows in the table. For example, table1 405 could contain the primary key field ID, which could uniquely identify each patient episode row in table1 405; for table2 410, the ROW_ID field values uniquely identify each row. A foreign key is a column in a table that does not uniquely identify rows in that table, but is used as a link to matching columns in other tables. For example, table2 410 could contain the foreign key field P_ID, which links back to the ID field in table1 405. This relationship between the two tables, referred to in the art as a one-to-many relationship, ensures that records in table1 405 may have one or more related records in table2 410, but each record in table2 410 is related to only one record in table1 405. In one embodiment, the E_COMP field may be used to store a status value for each record to denote whether the given patient episode data (in Table2 410) or all patient episode data (in Table1 405) were either complete or incomplete.

Figure 4B:
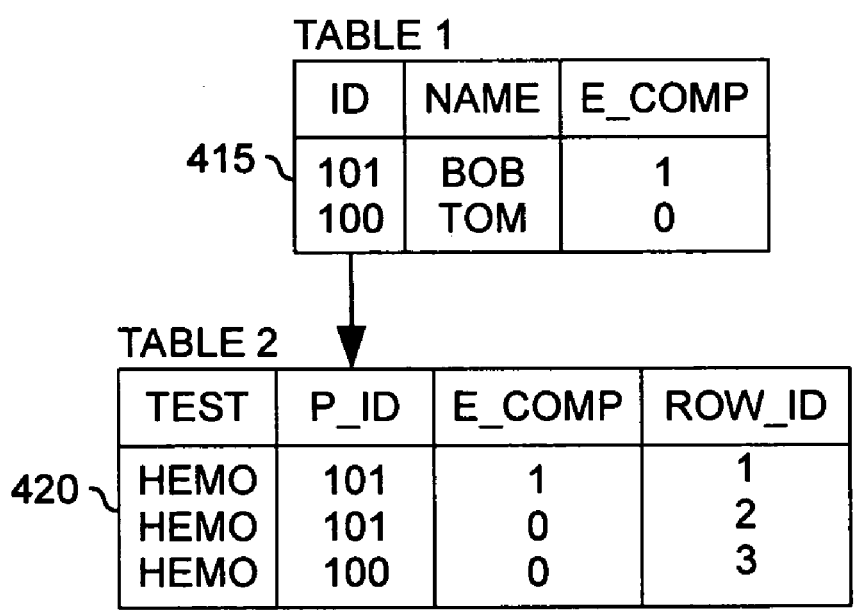
FIG. 4b is an exemplary view of two database tables.

FIG. 4b illustrates two exemplary populated tables (415 and 420) for hypothetical patients, Tom and Bob. The populated tables 415, 420 correspond to the schema 400 of the first table 405 and second table 410, respectively, of FIG. 4a. The new patient, Tom, (ID 100 in Table1 415) is having his first episode with the institution, as evidenced by the presence of only one corresponding row in Table2 420 where P_ID equals 100. Tom has had a hemoglobin test run (ROW_ID 3 in Table2 420) which is not a complete episode at this point. The incomplete status of the hemoglobin test run is shown in this example by the value of 0 in the E_COMP field of Table2 420. In contrast, patient Bob (ID 101 in Table1 415) has been through episodes before, as evidenced by a row in Table2 420 with the P_ID of 101 and a completed E_COMP value of 1. Bob also has an ongoing episode with the medical institution (ROW_ID 2 in Table2 420) with an incomplete status value of 0 in the E_COMP field of Table2 420. Thus, incomplete episodes are represented with E_COMP values of 0, which are changed to values of 1 once the corresponding episode is complete.

Abstract Querying in the Environment

Figure 5A:
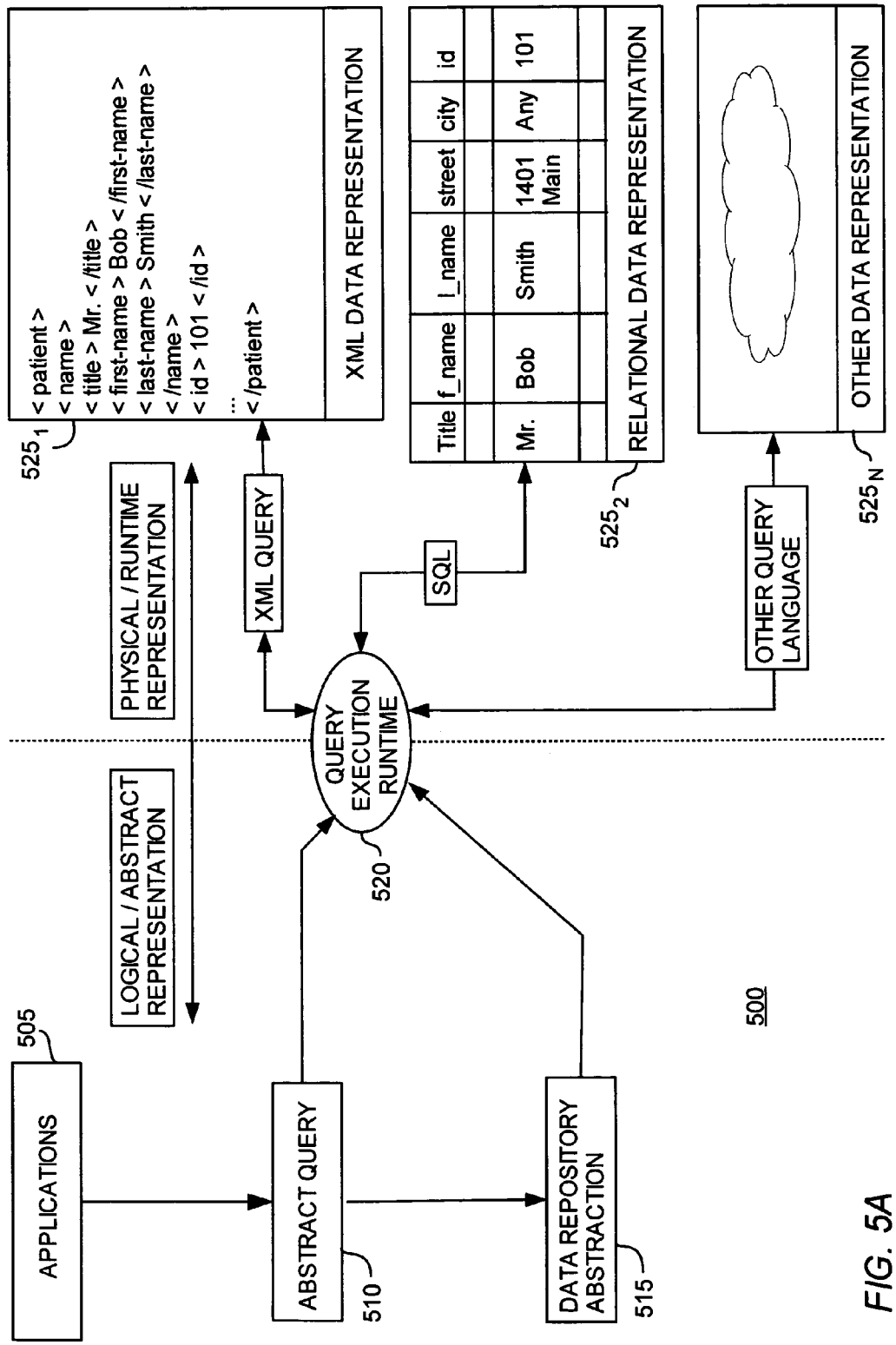
FIG. 5a is a relational view of software components of one embodiment of the invention.
Figure 5B:
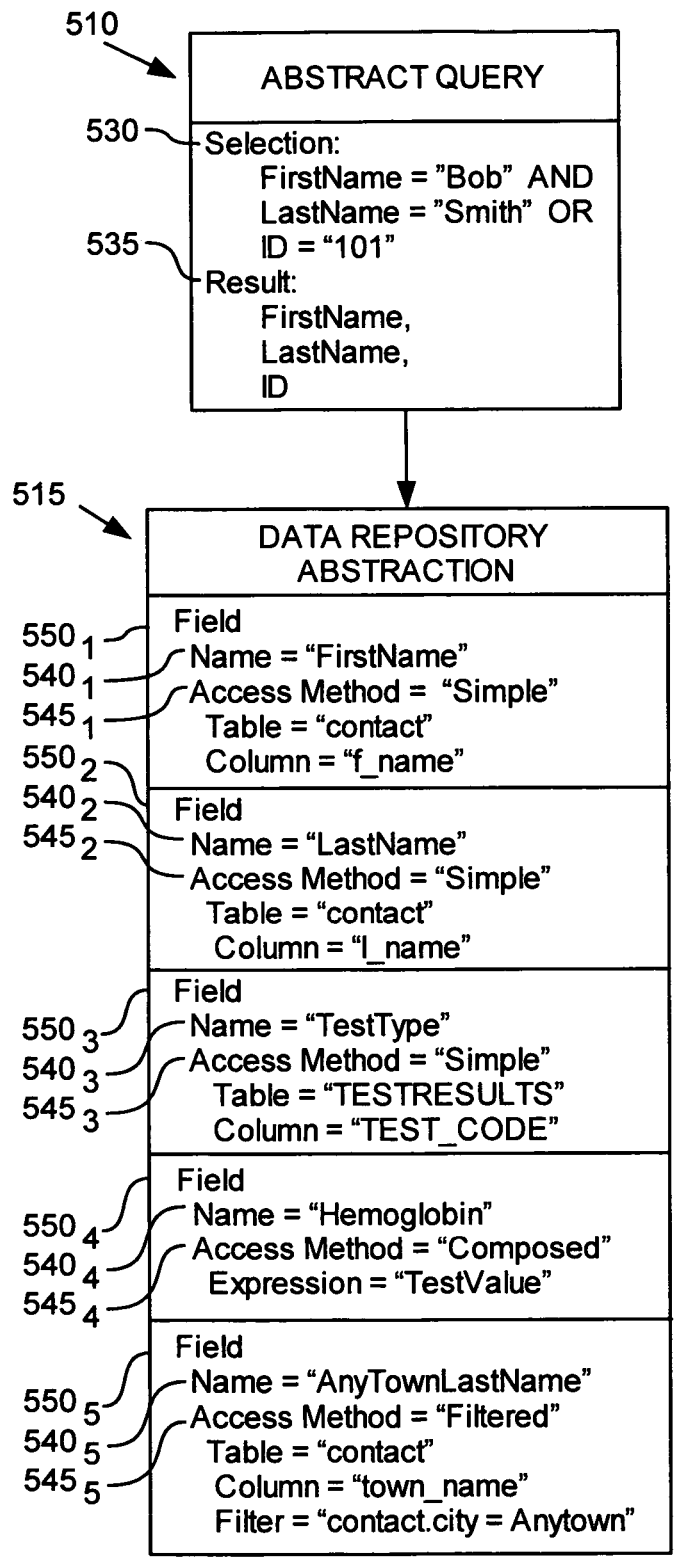
FIG. 5b is a relational view of software components of one embodiment of the invention.

In one embodiment, it may be desirable to query the episodic data contained in the medical information repository database using an abstraction framework. Generally, an abstraction framework may facilitate querying the data since the physical data is "decoupled" from the logical manner in which it is exposed to the user, thereby allowing the user to view the data in a simplified, more intuitive way. FIGS. 5A-B show an illustrative relational view of an abstraction environment 500 according to one embodiment of the invention. Reference is also made to FIG. 1, including the database 160 which may be the medical information repository database containing the episodic data (complete and incomplete). The requesting entity (e.g., one of the applications 505) issues a query 510 as defined by the respective application of the requesting entity. The queries issued by the applications 505 are defined according to an application query included with each application 505. The queries issued by the applications 505 may be predefined (i.e., hard coded as part of the applications 505) or may be generated in response to input (e.g., user input). In either case, the queries (referred to herein as "abstract queries") are composed using logical fields defined by the abstract query 510. In particular, the logical fields used in the abstract queries are defined by a data repository abstraction component 515 of the abstract query 510.

The resulting query 520 is generally referred to herein as an "abstract query" because the query is composed according to abstract (i.e., logical) fields rather than by direct reference to the underlying physical data entities in the database 160. As a result, abstract queries may be defined that are independent of the particular underlying data representation used. In one embodiment, the application query 510 may include both criteria used for data selection (selection criteria 530) and an explicit specification of the fields to be returned (return data specification 535) based on the selection criteria 530.

The logical fields specified by the application query 510 and used to compose the abstract query 520 are defined by the data repository abstraction component 515. In general, the data repository abstraction component 515 exposes information as a set of logical fields that may be used within a query (e.g., the abstract query 510) issued by the application 505 to specify criteria for data selection and specify the form of result data returned from a query operation. The logical fields are defined independently of the underlying data representation being used in the database 160, thereby allowing queries to be formed that are loosely coupled to the underlying data representation.

In general, the data repository abstraction component 515 comprises a plurality of field specifications $550_1$, $550_2$, $550_3$, $550_4$ and $550_5$ (five shown by way of example), collectively referred to as the field specifications 550. Specifically, a field specification is provided for each logical field available for composition of an abstract query. Each field specification comprises a logical field name $540_1$, $540_2$, $540_3$, $540_4$, $540_5$ (collectively, field name 540) and an associated access method $545_1$, $545_2$, $545_3$, $545_4$, $545_5$ (collectively, access method 545). The access methods associate (i.e., map) the logical field names to a particular physical data representation $525_1$, $525_2$ ... $525_N$ in a database (e.g., database 160). By way of illustration, two data representations are shown, an XML data representation $525_1$, and a relational data representation $525_2$. However, the physical data representation $525_N$ indicates that any other data representation, known or unknown, is contemplated. In one embodiment, a single data repository abstraction component 515 contains field specifications (with associated access methods) for two or more physical data representations 525. In an alternative embodiment, a different single data repository abstraction component 515 is provided for each separate physical data representation 525.

Any number of access methods are contemplated depending upon the number of different types of logical fields to be supported. In one embodiment, access methods for simple fields, filtered fields and composed fields are provided. The field specifications $550_1$, $550_2$ and $550_5$ exemplify simple field access methods $545_1$, $545_2$, and $545_5$, respectively. Simple fields are mapped directly to a particular entity in the underlying physical data representation (e.g., a field mapped to a given database table and column). By way of illustration, the simple field access method $545_1$, shown in FIG. 5B maps the logical field name $540_5$, ("FirstName") to a column named "f_name" in a table named "contact". The field specification $550_5$ exemplifies a filtered field access method $545_5$. Filtered fields identify an associated physical entity and provide rules used to define a particular subset of items within the physical data representation. An example is provided in FIG. 5B in which the filtered field access method $545_5$ maps the logical field name $540_5$ ("AnytownLastName") to a physical entity in a column named "town_name" in a table named "contact" and defines a filter for individuals in the city of Anytown. Another example of a filtered field is a New York ZIP code field that maps to the physical representation of ZIP codes and restricts the data only to those ZIP codes defined for the state of New York. The field specification $550_4$ exemplifies a composed field access method $545_4$. Composed access methods compute a logical field from one or more physical fields using an expression supplied as part of the access method definition. In this way, information which does not exist in the underlying data representation may be computed. In the example illustrated in FIG. 5B the composed field access method $545_4$ maps the logical field name $540_4$ "TestType" to "TestValue". Another example is a sales tax field that is composed by multiplying a sales price field by a sales tax rate.

It is contemplated that the formats for any given data type (e.g., dates, decimal numbers, etc.) of the underlying data may vary. Accordingly, in one embodiment, the field specifications 550 include a type attribute which reflects the format of the underlying data. However, in another embodiment, the data format of the field specifications 550 is different from the associated underlying physical data, in which case an access method is responsible for returning data in the proper format assumed by the requesting entity. Thus, the access method must know what format of data is assumed (i.e., according to the logical field) as well as the actual format of the underlying physical data. The access method can then convert the underlying physical data into the format of the logical field.

By way of example, the field specifications 550 of the data repository abstraction component 515 shown in FIG. 5b are representative of logical fields mapped to data represented in the relational data representation $525_2$. However, other instances of the data repository extraction component 515 map logical fields to other physical data representations, such as XML.

An illustrative abstract query corresponding to the abstract query 510 shown in FIG. 5a is shown in Table 1 below. By way of illustration, the Data Repository Abstraction 515 is defined using XML. However, any other language may be used to advantage.

TABLE 1

QUERY EXAMPLE

| | |
|---|---|
| 001 | <?xml version="1.0"?> |
| 002 | <field name="TestType"> |
| 003 |   <accessmethod> |

TABLE 1-continued

QUERY EXAMPLE

| | |
|---|---|
| 004 |     <simple attrname="TEST_CODE" |
| |     entityName="TESTRESULTS" /> |
| 005 |   </accessmethod> |
| 006 | </field> |
| 007 | <field> |
| 008 |   <accessmethod> |
| 009 |     <simple attrname="numeric_value" |
| |     entityName="TESTRESULTS" /> |
| 010 |   </accessmethod> |
| 011 |   <type baseType="float" /> |
| 012 |   <description>Internal Generic Test Value Field</description> |
| 013 | </field> |
| 014 | <fieldtemplate Name="Hemogloblin"> |
| 015 |   <accessmethod> |
| 016 |     <composed> |
| 017 |       <composition>DECIMAL(<fieldref name= "data://Internal/TestValue"/>, |
| 018 |       15,3)</composition> |
| 019 |     <where> |
| 020 |       <condition field="data://Internal/TestType" operator="EQ"> |
| 021 |         <value val="32-2320" /> |
| 022 |       </condition> |
| 023 |     </where> |
| 024 |     </composed> |
| 025 |   </accessmethod> |
| 026 |   <type baseType="float" /> |
| 027 |   <description>Hemoglobin Test</description> |
| 028 | <fieldtemplate> |

Illustratively, the abstract query shown in Table 1 includes a selection specification (lines 014-028) containing selection criteria (lines 019-023). In one embodiment, a selection criterion consists of a field name (for a logical field), a comparison operator (=,>,<, etc) and a value expression (what is the field being compared to). In one embodiment, result specification is a list of abstract fields that are to be returned as a result of query execution. A result specification in the abstract query may consist of a field name and sort criteria.

Figure 6:
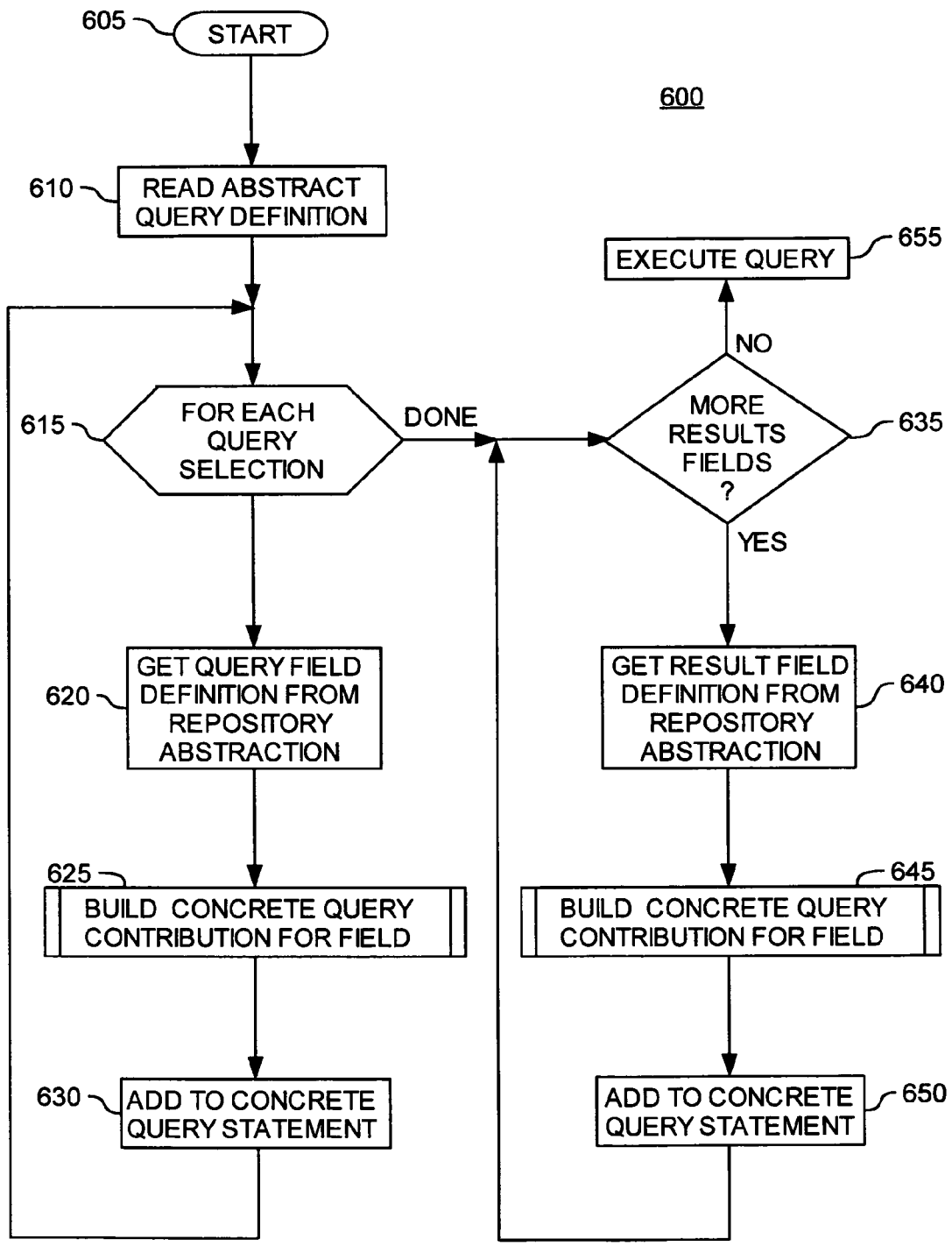
FIG. 6 is a flow chart illustrating the operation of a runtime component.

FIG. 6 shows an illustrative runtime method 600 exemplifying one embodiment of an operation of a runtime component. The method is entered at step 605 when the runtime component receives as input an instance of an abstract query (such as the abstract query 510 shown in FIG. 5). At step 610, the runtime component reads and parses the instance of the abstract query and locates individual selection criteria and desired result fields. At step 615, the runtime component enters a loop (comprising steps 615, 620, 625 and 630) for processing each query selection criteria statement present in the abstract query, thereby building a data selection portion of a Concrete Query. In one embodiment, a selection criterion consists of a field name (for a logical field), a comparison operator (=, >, <, etc) and a value expression (what is the field being compared to). At step 620, the runtime component uses the field name from a selection criterion of the abstract query to look up the definition of the field in the data repository abstraction 515. As noted above, the field definition includes a definition of the access method used to access the physical data associated with the field. The runtime component then builds (step 625) a Concrete Query Contribution for the logical field being processed. As defined herein, a Concrete Query Contribution is a portion of a concrete query that is used to perform data selection based on the current logical field. A concrete query is a query represented in languages like SQL and XML Query and is consistent with the data of a given physical data repository (e.g., a relational database or XML repository). Accordingly, the concrete query is used to locate and retrieve data from the physical data repository, represented by the database 160 shown in FIG. 1. The Concrete Query Contribution generated for the current field is then added to a Concrete Query Statement 630. The method 600 then returns to step 615 to begin processing for the next field of the abstract query. Accordingly, the process entered at step 615 is iterated for each data selection field in the abstract query, thereby contributing additional content to the eventual query to be performed.

After building the data selection portion of the concrete query, the runtime component identifies the information to be returned as a result of query execution. As described above, in one embodiment, the abstract query defines a list of abstract fields that are to be returned as a result of query execution, referred to herein as a result specification. A result specification in the abstract query may consist of a field name and sort criteria. Accordingly, the method 600 enters a loop at step 635 (defined by steps 635, 640, 645 and 650) to add result field definitions to the concrete query being generated. At step 640, the runtime component looks up a result field name (from the result specification of the abstract query) in the data repository abstraction 515 and then retrieves a Result Field Definition from the data repository abstraction 515 to identify the physical location of data to be returned for the current logical result field. The runtime component then builds (as step 645) a Concrete Query Contribution (of the concrete query that identifies physical location of data to be returned) for the logical result field. At step 650, Concrete Query Contribution is then added to the Concrete Query Statement. Once each of the result specifications in the abstract query has been processed, the query is executed at step 655.

Figure 7:
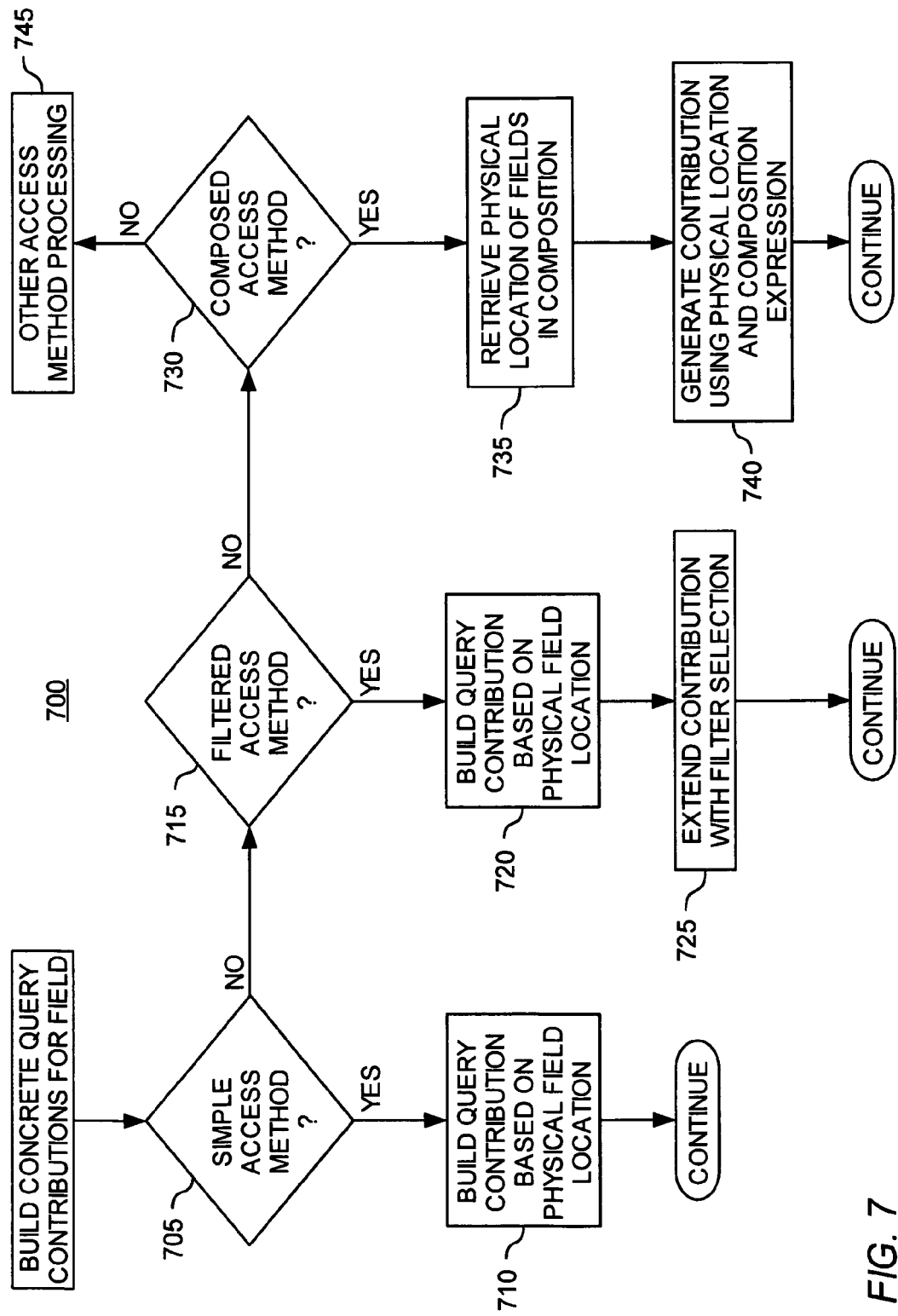
FIG. 7 is a flow chart illustrating the operation of a runtime component.

One embodiment of a method 700 for building a Concrete Query Contribution for a logical field according to steps 640 and 645 is described with reference to FIG. 7. At step 705, the method 700 queries whether the access method associated with the current logical field is a simple access method. If so, the Concrete Query Contribution is built (step 710) based on physical data location information and processing then continues according to method 700 described above. Otherwise, processing continues to step 715 to query whether the access method associated with the current logical field is a filtered access method. If so, the Concrete Query Contribution is built (step 720) based on physical data location information for some physical data entity. At step 725, the Concrete Query Contribution is extended with additional logic (filter selection) used to subset data associated with the physical data entity. Processing then continues according to method 700 described above.

If the access method is not a filtered access method, processing proceeds from step 715 to step 730 where the method 700 queries whether the access method is a composed access method. If the access method is a composed access method, the physical data location for each sub-field reference in the composed field expression is located and retrieved at step 735. At step 735, the physical field location information of the composed field expression is substituted for the logical field references of the composed field expression, whereby the Concrete Query Contribution is generated. Processing then continues according to method 700 described above.

If the access method is not a composed access method, processing proceeds from step 730 to step 745. Step 745 is representative of any other access methods types contemplated as embodiments of the present invention. However, it should be understood that embodiments are contemplated in which less then all the available access methods are implemented. For example, in a particular embodiment only simple access methods are used. In another embodiment, only simple access methods and filtered access methods are used.

As described above, it may be necessary to perform a data conversion if a logical field specifies a data format different from the underlying physical data. In one embodiment, an initial conversion is performed for each respective access method when building a Concrete Query Contribution for a logical field according to the method 700. For example, the conversion may be performed as part of, or immediately following, the steps 710, 720 and 725. A subsequent conversion from the format of the physical data to the format of the logical field is performed after the query is executed at step 655. Of course, if the format of the logical field definition is the same as the underlying physical data, no conversion is necessary.

In various embodiments, numerous advantages are provided by the above-described abstraction model. In one aspect, advantages are achieved by defining a loose coupling between the application query specification and the underlying data representation. Rather than encoding an application with specific table, column and relationship information, as is the case where SQL is used, the application defines data query requirements in a more abstract fashion that are then bound to a particular physical data representation at runtime. The loose query-data coupling of the present invention enables requesting entities (e.g., applications) to function even if the underlying data representation is modified or if the requesting entity is to be used with a completely new physical data representation than that used when the requesting entity was developed. In the case with a given physical data representation is modified or restructured, the corresponding data repository abstraction is updated to reflect changes made to the underlying physical data model. The same set of logical fields are available for use by queries, and have merely been bound to different entities or locations in physical data model. As a result, requesting entities written to the abstract query interface continue to function unchanged, even though the corresponding physical data model has undergone significant change. In the event a requesting entity is to be used with a completely new physical data representation than that used when the requesting entity was developed, the new physical data model may be implemented using the same technology (e.g., relational database) but following a different strategy for naming and organizing information (e.g., a different schema). The new schema will contain information that may be mapped to the set of logical fields required by the application using simple, filtered and composed field access method techniques. Alternatively, the new physical representation may use an alternate technology for representing similar information (e.g., use of an XML based data repository versus a relational database system). In either case, existing requesting entities written to use the abstract query interface can easily migrate to use the new physical data representation with the provision of an alternate data repository abstraction which maps fields referenced in the query with the location and physical representation in the new physical data model.

In another aspect, the abstraction model facilitates ease-of-use for the application builder and the end-user. Use of an abstraction layer to represent logical fields in an underlying data repository enables an application developer to focus on key application data requirements without concern for the details of the underlying data representation. As a result, higher productivity and reduced error rates are achieved during application development. With regard to the end user, the data repository abstraction provides a data filtering mechanism, exposing pertinent data and hiding nonessential content that is not needed by a particular class end-user developing the given query.

It should be noted that any reference herein to particular values, definitions, programming languages and examples is merely for purposes of illustration. Accordingly, the invention is not limited by any particular illustrations and examples. Further, while aspects of the invention are described with reference to SELECTION operations, other input/output operation are contemplated, including well-known operations such as ADD, MODIFY, INSERT, DELETE and the like. Of course, certain access methods may place restrictions on the type of abstract query functions that can be defined using fields that utilize that particular access method. For example, fields involving composed access methods are not viable targets of MODIFY, INSERT and DELETE.

In one embodiment, the abstraction framework could be used to create abstract queries for the purpose of obtaining information from the MIR database 255 (components described above with reference will be identified by like reference numbers). Utilizing the abstraction framework would allow applications 265 to query the MIR database 255 without having to understand the underlying MIR database 255 schema. This abstraction framework design could allow for the creation of a plurality of sniffers into the MIR database 255. Since the MIR database 255 would have a normalized database schema that utilized the abstraction framework, sniffer creation would be far more efficient since each sniffer could be written against the same abstracted schema, instead of having to create a different sniffer for each non-lized normalized datastore 225.

In an environment that uses an abstraction framework like the one described above any field can be given a condition that will be applied when the field is used. For example, a field for a hemoglobin test is shown in Table 2 below:

TABLE 2

CONDITION EXAMPLE

```
001   <?xml version="1.0"?>
002   <field name="TestType">
003      <accessmethod>
004         <simple attrname="TEST_CODE" entityName=
            "TESTRESULTS" />
005      </accessmethod>
006      <type baseType="float" />
007   </field>
008   <field name="TestValue">
009      <accessmethod>
010         <simple attrname="numeric_value" entityName=
            "TESTRESULTS" />
011      </accessmethod>
012      <type baseType="float" />
013      <description>Internal Generic Test Value Field</description>
014   </field>
015   <fieldtemplate Name="Hemoglobin">
016      <accessmethod>
017         <composed>
018            <composition>DECIMAL(<fieldref name=
               "data://Internal/TestValue"/>,
019               15,3)</composition>
020            <where>
021               <condition field="data://Internal/TestType"
                  operator="EQ">
022                  <value val="32-2320" />
023               </condition>
024            </where>
025         </composed>
026      </accessmethod>
027      <type baseType="float" />
028      <description>Hemoglobin Test</description>
029   </fieldtemplate>
```

Based on the field above, a value is accessed from the numeric_value column of the TESTRESULTS table. It is further specified that to be a hemoglobin test value, the accessed value of the TEST_CODE column must be 32-2320. This field definition of the abstraction model can be further augmented with additional conditions to account for episodes. For example, a pending (incomplete) hemoglobin test can be written as show in Table 3 (only the hemoglobin field and episode field are shown—the TestType and TestValue are reused from above):

TABLE 3

PENDING HEMOGLOBIN FIELD EXAMPLE

```
001   <field name="EpisodeComplete">
002      <accessmethod>
003         <simple attrname="EpisodeComplete"
            entityname="TESTRESULTS" />
004      </accessmethod>
005      <type basetype="char" />
006   </field>
007   <fieldtemplate name="Hemoglobin">
008      <accessmethod>
009         <composed>
010   <composition>DECIMAL(<fieldref name=
      "data://Internal/TestValue"
011   />,15,3)</composition>
012            <where>
013               <condition operator="AND">
014                  <condition field=
                     "data://Internal/TestType"
                     operator="EQ">
015                     <value val="32-2320" />
016                  </condition>
017                  <condition field=
                     "data://Internal/EpisodeComplete"
                     operator="EQ">
018                     <value val="0" />
019                  </condition>
020               </condition>
021            </where>
022         </composed>
023      </accessmethod>
024      <type basetype="float" />
025      <description>Hemoglobin Test</description>
026   </fieldtemplate>
```

The option now exists for using the above fields in arbitrary ways to navigate the data via the abstraction framework. For example, two sets of categories can be created as shown in Table 4:

TABLE 4

ABSTRACTION CATEGORY EXAMPLE

```
001   <root>
002      <pending episodes>
003         <fields for pending episodes - these have where
            EpisodeComplete = 0
004      condition>
005      <complete episodes>
006         <field for complete episodes - these have where
            EpisodeComplete=1
007      condition>
```

The example in Table 4 defines two categories, one for complete episodes and another for incomplete episodes. This categorization allows a user to navigate and view data according to these two defined categories, regardless of the specific events to which the data are related (i.e., hemoglobin test values, testicular cancer test values, etc.). In an alternative embodiment, the abstraction framework allows a user to navigate and view the data according to hemoglobin test values (top level (parent) node) that are grouped (sublevel (child)

nodes) according to complete and incomplete episode data. In any case, the provision of such an infrastructure allows the composition of queries to find relevant records and expose the status of those records. If records are found by an appropriately configured sniffer (configured on the basis of an abstraction framework, such as the one described above), action can be taken on those records. Exemplary actions would include canceling, modifying or alerting appropriate clinical staff about a potential drug conflict or lack of effectiveness of a prescribed drug based on historical data or gene expression data, or alerting clinical researchers about a new prospective client that fits their research criteria given new incoming diagnosis information.

CONCLUSION

By providing for the importation of episode data (e.g., health-related episode data) into an operational datastore and maintaining a status object for the data, embodiments of the present invention allow a user to retrieve more recent and perhaps time-critical information while still being informed as to the status of the episode data. As a result, the user may be allowed to perform a more efficient, timely, and effective query to the operational datastore. Further, by the provision of an abstraction framework, abstract queries may be employed to facilitate a more intuitive type of querying that does not require user to understand the underlying physical schema, and may facilitate creation of data sniffers.

While the foregoing is directed to embodiments of the present invention, other and further embodiments of the invention may be devised without departing from the basic scope thereof, and the scope thereof is determined by the claims that follow.

What is claimed is:

1. A computer-implemented method for storing status-designated health-related episode data comprising configuring one or more processors to perform an operation comprising:
providing a database which stores health-related episode data from a plurality of data sources, wherein each of the plurality of data sources stores a portion of the health-related episode data as a different data format; wherein the episode data includes data for complete episodes and incomplete episodes, an episode containing data for a plurality of related medical events, such that an incomplete episode is missing, from the database, data for at least one of the related medical events and a complete episode includes, in the database, data for all of the plurality of related medical events;
for each of the incomplete episodes, receiving a plurality of updates from the plurality of data sources;
normalizing the data received in the updates to conform to a common schema;
evaluating, by operation of the one or more computer processors, the stored health-related episode data and the data received in the updates from the plurality of data sources to determine an appropriate status for each of the incomplete episodes as a result of the updates; and
for each of the plurality of updates, designating a status of the episode data being updated in the database, the status indicating that the episode data being updated is complete or incomplete, based on the respective determined appropriate status;
wherein evaluating the stored health-related episode data and the data received in the updates from the plurality of data sources to determine an appropriate status for each of the incomplete episodes as a result of the updates comprises:
identifying stored health-related episode data that is part of the same episode as the data received in the updates; and
determining, for at least one of the incomplete episodes and by operation of the one or more computer processors, an appropriate status of incomplete upon determining that the data received in the updates is a portion of an episode for which partial episodic data is found in the stored health-related episode data, but which does not complete the episode.

2. The computer-implemented method of claim 1, wherein the operation further comprises, for each update from a given data source, shredding the data of the received update in order to normalize the data.

3. The computer-implemented method of claim 1, wherein statuses of the episode data for both complete and incomplete episodes are stored in a status object.

4. The computer-implemented method of claim 3, wherein the operation further comprises, in response to receiving at least some of the updates, modifying the status object to reflect one of a complete status and an incomplete status for each episode.

5. The computer-implemented method of claim 1, wherein the operation further comprises:
providing a data abstraction model that models the episode data;
wherein the data abstraction model comprises a plurality of logical field definitions, each of the definitions comprising a logical field name, at least one location attribute identifying a location of episode data corresponding to the logical field name, and a reference to an access method selected from at least two different access method types; and
wherein each of the different access method types defines a different manner of exposing the episode data corresponding to the logical field name of the respective logical field definition.

6. The computer-implemented method of claim 5, wherein the operation further comprises providing a query specification, defining an interface to the plurality of logical field definitions thereby allowing abstract queries to be composed on the basis of the plurality of logical field definitions.

7. The computer-implemented method of claim 1, wherein evaluating the stored health-related episode data and the data received in the updates from the plurality of data sources to determine an appropriate status for each of the incomplete episodes as a result of the updates comprises:
determining, for each of the incomplete episodes and by operation of the one or more computer processors, an appropriate status of incomplete upon determining that the data received in the updates is a first portion of an episode.

8. The computer-implemented method of claim 1, wherein evaluating the stored health-related episode data and the data received in the updates from the plurality of data sources to determine an appropriate status for each of the incomplete episodes as a result of the updates comprises:
identifying stored health-related episode data that is part of the same episode as the data received in the updates; and
determining, for each of the incomplete episodes and by operation of the one or more computer processors, an appropriate status of complete upon determining that the data received in the updates is a final portion of an episode for which partial episodic data is found in the stored health-related episode data.

9. The computer-implemented method of claim 1, wherein the operation further comprises:
analyzing, by a sniffer, the normalized data received in the updates from the plurality of data sources and having designated statuses to perform a predefined action upon determining that a predefined condition is satisfied.

* * * * *